(12) United States Patent
Edvardsen et al.

(10) Patent No.: US 8,409,158 B2
(45) Date of Patent: Apr. 2, 2013

(54) OSTOMY APPLIANCE WITH A LEAKAGE INDICATOR

(75) Inventors: Henrik Edvardsen, Copenhagen N (DK); Michael Hansen, Gilleleje (DK); Danuta Ciok, Nivaa (DK); Lene Feldskov Nielsen, Copenhagen K (DK); Kent Hoeier Nielsen, Oelstykke (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/382,527

(22) PCT Filed: Jun. 22, 2010

(86) PCT No.: PCT/DK2010/050153
§ 371 (c)(1),
(2), (4) Date: Feb. 24, 2012

(87) PCT Pub. No.: WO2011/003421
PCT Pub. Date: Jan. 13, 2011

(65) Prior Publication Data
US 2012/0143155 A1 Jun. 7, 2012

(30) Foreign Application Priority Data

Jul. 7, 2009 (DK) ................................. 2009 70055
Jul. 7, 2009 (DK) ................................. 2009 70056

(51) Int. Cl.
*A61F 5/44* (2006.01)
*A61F 13/00* (2006.01)
*A61F 13/02* (2006.01)
*A61F 5/443* (2006.01)
*A61M 1/00* (2006.01)

(52) U.S. Cl. ..................... 604/318; 604/65; 604/100.01; 604/100.02; 604/304; 604/307; 604/308; 604/325; 604/332; 604/335; 604/337; 604/338; 604/355; 604/361; 604/378; 604/380

(58) Field of Classification Search ........................ None
See application file for complete search history.

(56) References Cited

U.S. PATENT DOCUMENTS 5,942,186 A 8/1999 Sanada et al.

FOREIGN PATENT DOCUMENTS

| WO | 2006109034 | 10/2006 |
| WO | 2007098762 | 9/2007 |
| WO | WO 2007121744 A1 * | 11/2007 |

* cited by examiner

*Primary Examiner* — Melanie Hand
*Assistant Examiner* — Joshua Lee
(74) *Attorney, Agent, or Firm* — Coloplast Corp., Coloplast A/S; Daniel G. Chapik; Nicholas R. Baumann

(57) ABSTRACT

An ostomy device that comprises an adhesive wafer for attaching to the skin around the stoma. The wafer comprises an adhesive layer having a proximal adhesive side and a distal side, where the distal side is covered with a backing layer. The wafer comprises a central portion and a peripheral portion, and it comprises a proximal section located on the proximal side of the central portion and a distal section visually arranged on the distal side of peripheral portion, wherein the distal section changes colour when the proximal section is exposed to fluid.

11 Claims, 2 Drawing Sheets

OSTOMY APPLIANCE WITH A LEAKAGE INDICATOR

BACKGROUND OF THE INVENTION

1. Field of the Invention

The invention relates to an ostomy appliance with a leakage indicator.

Body attachments for collecting body fluids often have leakage issues. The sources of leakage can be many, for example poor product performance, extended wear time, wrong choice of product for the task, or incorrect application and use. Leakage may cause soiled clothes, psychological discomfort and inconvenience, but also more severe issues like infections and skin disorders.

Many products and accessories intended for collecting body fluids are available, and the selection of the right combination for the individual solutions can in many cases reduce the likelihood of leakage.

Devices with electronic leakage detection enable various advanced and complex solutions, however in terms of production costs, user interface complexity, regulatory complexity and the environmental issues related to disposal of electronic components that are integrated in disposable collecting devices, they are not optimal solutions.

2. Description of the Related Art

Different ways of detecting leakage or indicating time for change of the collecting device have been seen in prior solutions.

U.S. Pat. No. 5,942,186 discloses an adhesive plate with an indicator function, and an indicator therefore. The indicator is a hydrophilic composition that contains a water-soluble colouring matter, such as a food colour, a dye, a pigment or metallic salt applied onto or embedded in a part or the whole of a peripheral region of the plate that is spaced apart from the centre thereof. The water-soluble colouring matter is dissolvable in liquid excrements or exudates. It changes colour and provides visible indication of the end of the usable life of the adhesive plate.

EP 1 991 187 discloses a method for detecting detachment of a dressing, which is applied to a surface of an at least partly electrically conductive object. The dressing comprises an adhesive for attaching the dressing to the electrically conductive object and at least two electrodes arranged in a distance from the electrically conductive object. A voltage is applied to the first and second electrode establishing an electrical circuit comprising a first capacitor between the first electrode and the electrically conductive object, and a second capacitor between the second electrode and the electrically conductive object. The changes of the capacitance between at least one of the first and the second electrode, and the electrically conductive object are detected, and an alarm is activated when the changes of the capacitance reach a predetermined value.

However there is still a need for a device that is capable of indicating leakage of an ostomy device in a simple manner.

BRIEF DESCRIPTION OF THE DRAWINGS

The invention is disclosed in more detail with reference to the drawings in which.

DETAILED DESCRIPTION OF THE PRESENT INVENTION

Figure 1:
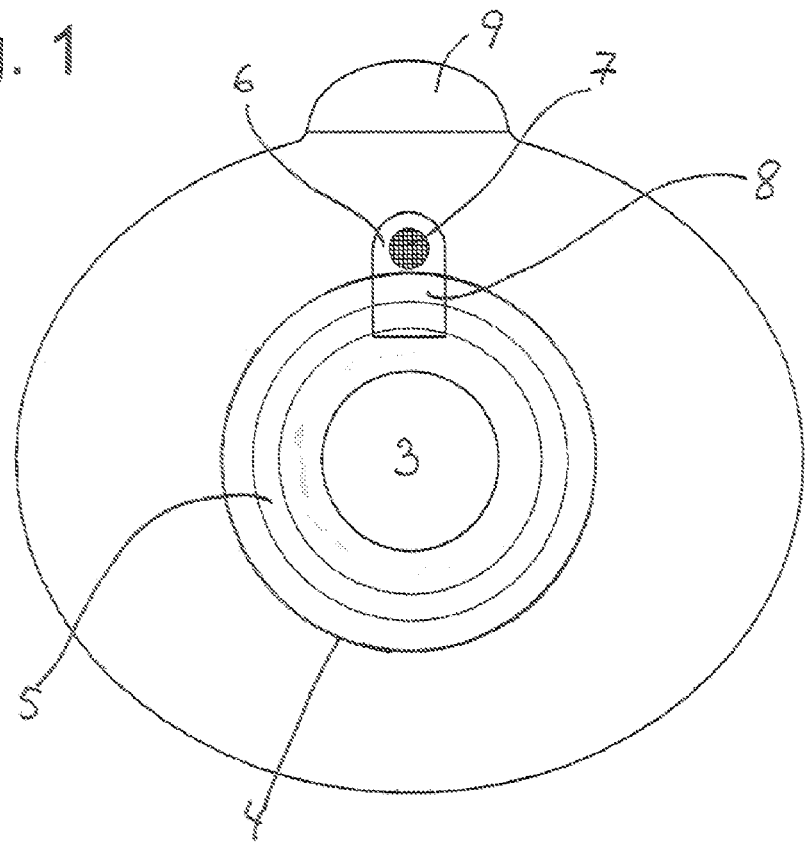
FIG. 1 shows a top view of a preferred embodiment of the invention.

The invention relates to an ostomy device comprising a collection bag and an adhesive wafer for attaching to the skin around the stoma, the wafer comprising an adhesive layer having a proximal adhesive side and a distal side, the distal side being covered with a backing layer, the wafer comprises a central portion being inside the bag and a peripheral portion being outside the bag, wherein the wafer comprises a proximal section located on the proximal side of the central portion and a distal section visually arranged on the distal side of peripheral portion, wherein the distal section changes colour when the proximal section is exposed to fluid.

By "proximal" is meant the portion closest to the skin, whereas by "distal" is meant the portion facing away from the skin.

By the phrase "central portion" is meant an area at the central portion of the wafer. "Central" should be interpreted as being in the middle portion of the wafer and not peripheral, but should not necessarily be symmetrically located on the wafer. The central portion of the wafer is provided with a hole for accommodating the stoma. The phrase "peripheral portion" should be understood as the portion encircling the central portion. The central portion and the peripheral portion are separated by a portion whereto a collection bag is attached or can be attached. During use, the central portion of the wafer is inside the collection bag, whereas the peripheral portion is outside the bag. The portion of the wafer being inside the bag is not directly accessible without removing the bag as it defines an inner wall portion of the bag, whereas the portion being outside the bag is directly accessible, independently of the presence of the bag.

A leakage is when effluent from the stoma migrates under the adhesive wafer leading to detachment of the adhesive from the skin in the affected area as well as maceration of the skin. The leak begins in the area near the stoma and may progress to the peripheral portion of the wafer, leading to detachment of the wafer and soiling of the surroundings. This situation is highly undesired, so there is a need for at way to determine a leakage at an early stage, leaving time for changing the wafer before the leakage has progressed too far.

When trying to diminish the risk of leakage between the skin and the adhesive wafer of an ostomy device, the main focus is normally on improving the adhesive part by improved materials and design. The present approach facilitates a simple and effective indicator of when there is an actual leakage and how progressed the leakage is.

This device does not require the use of electronics, and therefore the regulations and challenges related to this type of solution are not an issue. Furthermore, environmental aspects with regard to disposal of the device are diminished.

In order to detect signs of leakage as early as possible, the leakage indicator should be located close to the stoma that is at the central portion of the wafer. However, the central portion of the wafer is, when in use, covered by the collection bag, and therefore it is difficult to see a colour reaction through the bag indicating leakage. Placing the indicator on the peripheral portion of the wafer will make the colour reaction visible, but at by time the leakage has reached the peripheral portion of the wafer, the progression of the leakage is critical.

This ostomy device has leakage detection in the form of a proximal section that is located near the stoma at the central portion of the wafer, whereas the visual indication of the leakage is displayed on a distal section visibly located outside the bag, on the peripheral portion of the wafer. In this way, it is possible to detect leakage at an early stage and visualize it by a colour reaction accessible without removing the bag or looking into it.

The proximal section and the distal section may be connected via a communication passage.

Such a passage may be formed of a moisture transporting material such as a wicking material, or it may be formed of a chemical that reacts to fluid.

The communication passage may be in the form of a strip or a sheet, connecting the distal section with the proximal section. In one embodiment, the communication passage, the distal section and the proximal section constitute one piece.

The proximal section may be in the form of one or more discrete zones. This opens up for the possibility of detecting where on the wafer the leak is located as only the affected zones will react to the leakage.

In one embodiment, the proximal section encircles the hole for the stoma. Thus, any leakage progressing from the stoma is detected by the proximal section and gives rise to a colour reaction at the distal section. The proximal section may preferably be located from 1 mm to 25 mm from the edge of the hole for the stoma.

The distal section may be in the form of one or more patches at the peripheral portion of the wafer, or it may be in the form of a line at least partly encircling the peripheral portion. In one embodiment, the distal section constitutes the entire peripheral portion of the wafer. The distal section may be located between the backing layer and the adhesive layer, or it may be located on the distal side of the backing layer and provided with an impermeable cover layer.

The proximal section may be in direct contact with the skin, allowing rapid uptake of leakage fluid. Leakage usually occurs between the skin and the wafer and can thus rapidly be detected.

The distal section produces a colour reaction when the proximal section is exposed to fluid. This reaction may be induced by presence of any kind of moisture, such as perspiration and effluents from the stoma. The colour reaction may also be induced by reacting to specific components from the effluent of the stoma. This may reduce the risk of "false" indication, introduced by perspiration and not by leakage. Such selectivity may for example be obtained by incorporating components that are selective to for example specific enzymes, bacterial constituents or pH.

The device has a leakage detection point (the proximal section), and a leakage indicating point (the distal section), the leakage indicating point and the leakage detection point being spaced apart from each other, which facilitates visual indication of leakage at the central portion of the wafer, shown at the peripheral portion of the wafer.

The proximal section can be made of a variety of absorbent or moisture transporting materials such as non-woven, filter paper, textile, adhesive, hydrocolloids, polysaccharides or super absorbers such as acrylic acids or combinations thereof.

The distal section comprises at least one constituent that is capable of changing colour. The colour constituent may be any suitable material such as pH indicators, food colours, and so on. The colour changing constituent may be a part of an enzyme assay. The colour constituent may be non-toxic, but as it is not in direct skin-contact, this is not strictly necessary.

In one embodiment, the colour reaction is facilitated by having a dye covered with a non-transparent layer. When the dye is wetted, it will wet the non-transparent layer and colour it. Alternatively, the non-transparent layer may turn transparent when wet, thus revealing the coloured layer underneath.

The adhesive wafer may be provided with an "ear", a tab member arranged at the edge portion of the flange. The ear serves as a handle during application and during detachment of the wafer from the skin. The distal section may be located on the ear, having the advantage that the ear portion typically extends further than the collection bag, rendering the colour reaction easily visible.

The adhesive wafer comprises a backing layer on the non-skin facing surface. The backing layer may be any suitable layer, for example a polymer film, a non-woven, foam or a foamed film. The backing layer may be vapour and water impermeable or it may be water impermeable but vapour permeable. The backing layer may be any colour or it may be transparent or translucent, thus allowing the colour reaction of the distal section to be visible through the backing layer.

The adhesive layer of the wafer may be any suitable skin-friendly adhesive.

The wafer may further be provided with a tactile indicator, producing a tactile response to leakage, for example by producing a raised portion that can be perceived when touched upon. By having a zone of the wafer responding to absorption of moisture by producing a perceivable change, a tactile leakage indicator is present. The tactile indicator is discrete for the user, because it can be felt through clothes and/or the collection bag, and it is therefore not necessary to expose the device to check leak status.

By tactile is meant that a change in the texture of the distal side of the wafer can be sensed when touched upon with, for example, fingers or the hand. The change may be in the form of a change in the topography of the wafer surface, such as raised, lowered or lack of knobs or ridges, or by a change in softness.

The tactile indicator may be achieved by incorporating a material that changes property when exposed to moisture into one or more specific zones of the wafer. Examples of such materials are hydrocolloids, superabsorbent fibres, superabsorbent particles, alginates, polysaccharides or foam.

The change of thickness of the second zone when exposed to moisture should be perceptible, being at least 10%, 20%, 30%, 40%, 50%, 60%, 75% or 100% smaller or larger than the thickness of the second zone when dry.

The ostomy device may be a one piece device where a collection bag is inseparately attached to the wafer or it may be a two piece device where the wafer and the collection bag are provided with coupling means and can therefore be attached and detached to each others.

DESCRIPTION OF THE PREFERRED EMBODIMENTS

The invention is now explained in more detail with reference to the drawings.

Figure 2:
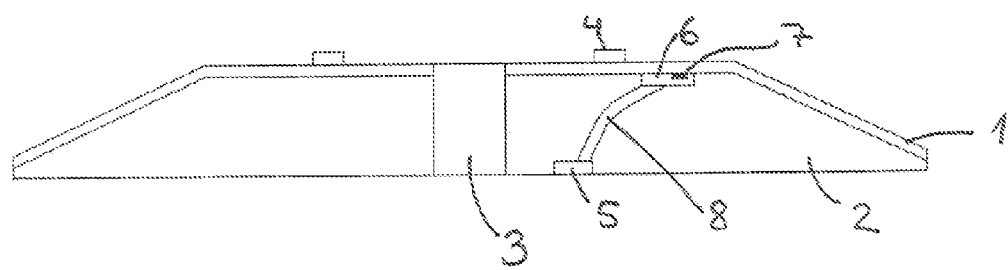
FIG. 2 shows a cross-section of the same embodiment.

FIG. 1 shows an embodiment comprising a wafer seen from the non-skin facing side. A cross-section of the same embodiment is shown in FIG. 2. The wafer comprises a backing layer (1), an adhesive layer (2) and a hole (3) for accommodating a stoma. A collection bag may be attached along an attachment portion (4). The bag is omitted from the drawing for clarity reasons. At the skin-facing/proximal surface of the central portion is a ring-shaped proximal section (5). At the peripheral portion of the wafer is located a distal section (6) comprising a colour indicator (7). The proximal section (5) and the distal section (6) are interconnected by a communication passage (8). The proximal section (5) is formed of a wicking material, absorbing fluid from any leakage, distributing the fluid over the ring-shaped proximal section (5) and thereby bringing it into contact with the communication passage (8). The passage (8) wicks the fluid from the proximal section (5) to the distal section (6), where it triggers a colour reaction (7). The wafer shown is provided with a tab member (9).

Figure 3:
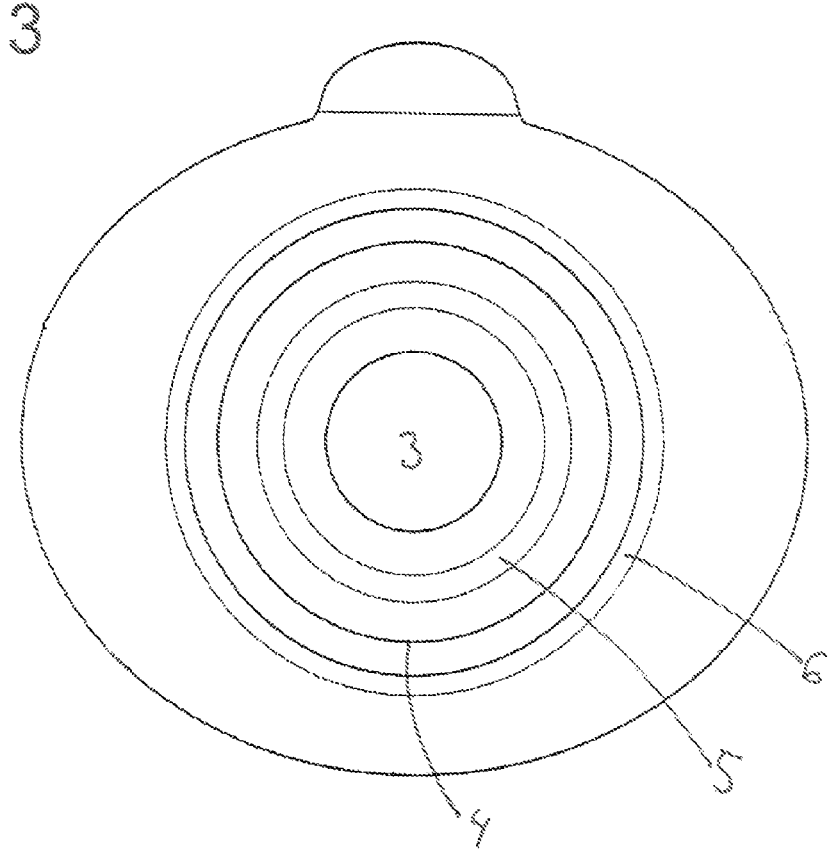
FIGS. 3 and 4 show another embodiment.
Figure 4:
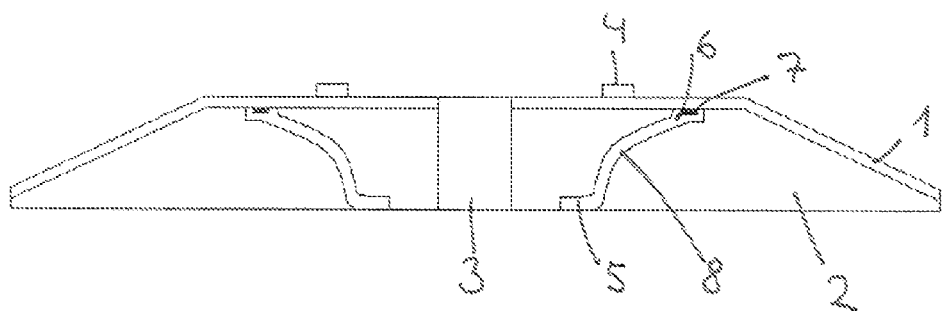

FIGS. 3 and 4 show another embodiment. In this embodiment, the proximal section (5), the communication passage (8) and at least a part of the distal section (6) constitute one sheet of circular wicking material. The inner periphery of the circular sheet, located at the central portion, is in contact with the skin, whereas the outer periphery of the sheet is located at the peripheral portion of the wafer. The distal section (6) further comprises an indicator (7) capable of changing colour when it is in contact with fluid from a leakage.

The invention claimed is:

1. An ostomy device attachable to a collection bag and comprising an adhesive wafer for attaching to skin around a stoma;
   a. the wafer comprising an adhesive layer having a proximal adhesive side and a distal side;
   b. the distal side being covered with a backing layer;
   c. the wafer comprises a central portion and a peripheral portion, the peripheral portion is located outside the collection bag when the adhesive wafer is attached to the collection bag,
      i. wherein the wafer comprises a proximal section located on the proximal adhesive side of the central portion and a distal section on the distal side of the peripheral portion,
      ii. wherein the distal section changes colour when the proximal section is exposed to fluid.

2. Ostomy device according to claim 1, wherein the proximal section and the distal section are connected via a communication passage.

3. Ostomy device according to claim 2, wherein the communication passage is formed of a wicking material.

4. Ostomy device according to claim 2, wherein the communication passage is in the form of a strip.

5. Ostomy device according to claim 2, wherein the communication passage is in the form of a sheet.

6. Ostomy device according to claim 2, wherein the communication passage is formed of a chemical that reacts to fluid.

7. Ostomy device according to claim 1, wherein the distal section is located on a tab member arranged at an edge portion of the wafer.

8. Ostomy device according to claim 1, wherein the proximal section is in the form of one or more discrete zones.

9. Ostomy device according to claim 1, wherein the distal section at least partly encircles the peripheral portion of the wafer.

10. Ostomy device according to claim 1, wherein the backing layer is transparent or translucent.

11. Ostomy device according to claim 1, wherein the wafer comprises a tactile leakage indicator.

* * * * *